(12) United States Patent
Pasch et al.

(10) Patent No.: US 12,230,402 B2
(45) Date of Patent: Feb. 18, 2025

(54) INJURY SEVERITY ESTIMATION BY USING IN-VEHICLE PERCEPTION

(71) Applicant: Intel Corporation, Santa Clara, CA (US)

(72) Inventors: Frederik Pasch, Karlsruhe (DE); Bernd Gassmann, Straubenhardt (DE); Kay-Ulrich Scholl, Malsch (DE); Cornelius Buerkle, Karlsruhe (DE); Fabian Oboril, Karlsruhe (DE)

(73) Assignee: Intel Corporation, Santa Clara, CA (US)

( * ) Notice: Subject to any disclaimer, the term of this patent is extended or adjusted under 35 U.S.C. 154(b) by 650 days.

(21) Appl. No.: 17/471,182

(22) Filed: Sep. 10, 2021

(65) Prior Publication Data

US 2021/0407687 A1 Dec. 30, 2021

(51) Int. Cl.
*B60Q 1/00* (2006.01)
*A61B 5/00* (2006.01)
(Continued)

(52) U.S. Cl.
CPC ............... *G16H 50/30* (2018.01); *A61B 5/18* (2013.01); *A61B 5/6893* (2013.01); *A61B 5/747* (2013.01); *B60W 30/08* (2013.01); *B60W 40/08* (2013.01); *B60W 50/14* (2013.01); *G06Q 50/265* (2013.01); *G06V 20/597* (2022.01);
(Continued)

(58) Field of Classification Search
CPC ........ G16H 50/30; G16H 40/67; G16H 50/70; G16H 50/20; A61B 5/18; A61B 5/6893; A61B 5/747; A61B 5/11; A61B 2503/22; B60W 30/08; B60W 40/08; B60W 50/14; B60W 2030/082; B60W 2420/40; B60W 2420/403; B60W 2420/408; B60W 2420/54; B60W 2540/221; B60W 2540/223; B60W 2540/227; B60W 2556/45; G06Q 50/265; G06V 20/597;
(Continued)

(56) References Cited

U.S. PATENT DOCUMENTS

| | | | |
|---|---|---|---|
| 8,825,277 B2 * | 9/2014 | Mcclellan | G06Q 10/06 701/34.2 |
| 9,718,468 B2 * | 8/2017 | Barfield, Jr. | G08G 1/16 |
| 11,126,917 B2 * | 9/2021 | Zerick | G16H 50/70 |

* cited by examiner

*Primary Examiner* — Toan N Pham
(74) *Attorney, Agent, or Firm* — Viering, Jentschura & Partner mbB

(57) ABSTRACT

A monitoring system may include a memory having computer-readable instructions stored thereon and a processor operatively coupled to the memory. The processor may read and execute the computer-readable instructions to perform or control performance of operations. The operations may include receive, prior to a collision involving a vehicle, sensor data representative of a feature of an internal environment and determine the collision has occurred. The operations may include automatically instruct, based on the collision, a sensor to generate another sensor data representative of another feature of the internal environment. The operations may include receive the another sensor data from the sensor and compare the sensor data and the another sensor data to accident data corresponding to previous accidents. The accident data may include a diagnosed injury and an accident severity of each of the previous accidents. The operations may include determine a severity of the collision based on the comparison.

20 Claims, 5 Drawing Sheets

(51) Int. Cl.
*A61B 5/18* (2006.01)
*B60W 30/08* (2012.01)
*B60W 40/08* (2012.01)
*B60W 50/14* (2020.01)
*G06Q 50/26* (2012.01)
*G06V 20/59* (2022.01)
*G08G 1/0962* (2006.01)
*G08G 1/16* (2006.01)
*G16H 40/67* (2018.01)
*G16H 50/30* (2018.01)
*G16H 50/70* (2018.01)

(52) U.S. Cl.
CPC ......... *G08G 1/09626* (2013.01); *G08G 1/164* (2013.01); *G16H 40/67* (2018.01); *G16H 50/70* (2018.01); *B60W 2030/082* (2013.01); *B60W 2420/40* (2013.01); *B60W 2420/403* (2013.01); *B60W 2420/408* (2024.01); *B60W 2420/54* (2013.01); *B60W 2540/221* (2020.02); *B60W 2540/223* (2020.02); *B60W 2540/227* (2020.02); *B60W 2556/45* (2020.02)

(58) Field of Classification Search
CPC .. G06V 40/103; G08G 1/09626; G08G 1/164; G08G 1/205
See application file for complete search history.

INJURY SEVERITY ESTIMATION BY USING IN-VEHICLE PERCEPTION

FIELD

The aspects discussed in the present disclosure are related to injury severity estimation by using in-vehicle perception.

BACKGROUND

Unless otherwise indicated in the present disclosure, the materials described in the present disclosure are not prior art to the claims in the present application and are not admitted to be prior art by inclusion in this section.

If a vehicle is involved in a collision, emergency responders may receive information regarding the vehicle and occupants. For example, the emergency responders may receive information indicating a number of occupants, a make or model of the vehicle, a location of the collision, odometry, or some combination thereof.

The subject matter claimed in the present disclosure is not limited to aspects that solve any disadvantages or that operate only in environments such as those described above. Rather, this background is only provided to illustrate one example technology area where some aspects described in the present disclosure may be practiced.

BRIEF DESCRIPTION OF THE DRAWINGS

Example aspects will be described and explained with additional specificity and detail through the use of the accompanying drawings in which.

DETAILED DESCRIPTION

Figure 1:
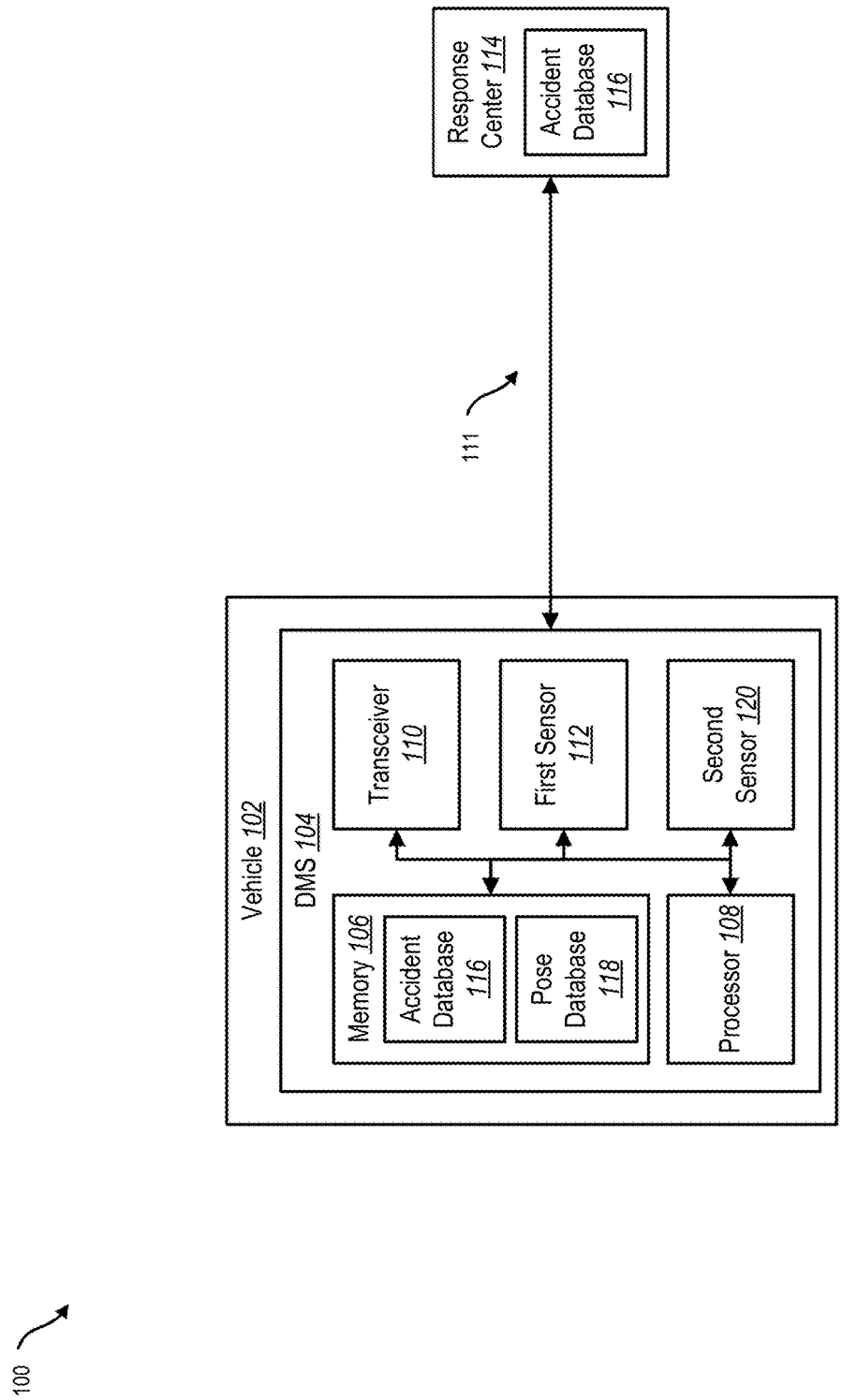
FIG. 1 illustrates a block diagram of an exemplary operational environment of a vehicle that includes a DMS to estimate a severity of an injury using in-vehicle perception.

The following detailed description refers to the accompanying drawings that show, by way of illustration, exemplary details in which aspects of the present disclosure may be practiced.

The word "exemplary" is used herein to mean "serving as an example, instance, or illustration". Any aspect or design described herein as "exemplary" is not necessarily to be construed as preferred or advantageous over other aspects or designs.

Throughout the drawings, it should be noted that like reference numbers are used to depict the same or similar elements, features, and structures, unless otherwise noted.

The phrase "at least one" and "one or more" may be understood to include a numerical quantity greater than or equal to one (e.g., one, two, three, four, [ . . . ], etc.). The phrase "at least one of" with regard to a group of elements may be used herein to mean at least one element from the group consisting of the elements. For example, the phrase "at least one of" with regard to a group of elements may be used herein to mean a selection of: one of the listed elements, a plurality of one of the listed elements, a plurality of individual listed elements, or a plurality of a multiple of individual listed elements.

The words "plural" and "multiple" in the description and in the claims expressly refer to a quantity greater than one. Accordingly, any phrases explicitly invoking the aforementioned words (e.g., "plural [elements]", "multiple [elements]") referring to a quantity of elements expressly refers to more than one of the said elements. For instance, the phrase "a plurality" may be understood to include a numerical quantity greater than or equal to two (e.g., two, three, four, five, [ . . . ], etc.).

The phrases "group (of)", "set (of)", "collection (of)", "series (of)", "sequence (of)", "grouping (of)", etc., in the description and in the claims, if any, refer to a quantity equal to or greater than one, i.e., one or more. The terms "proper subset", "reduced subset", and "lesser subset" refer to a subset of a set that is not equal to the set, illustratively, referring to a subset of a set that contains less elements than the set.

The term "data" as used herein may be understood to include information in any suitable analog or digital form, e.g., provided as a file, a portion of a file, a set of files, a signal or stream, a portion of a signal or stream, a set of signals or streams, and the like. Further, the term "data" may also be used to mean a reference to information, e.g., in form of a pointer. The term "data", however, is not limited to the aforementioned examples and may take various forms and represent any information as understood in the art.

The terms "processor" or "controller" as, for example, used herein may be understood as any kind of technological entity that allows handling of data. The data may be handled according to one or more specific functions executed by the processor or controller. Further, a processor or controller as used herein may be understood as any kind of circuit, e.g., any kind of analog or digital circuit. A processor or a controller may thus be or include an analog circuit, digital circuit, mixed-signal circuit, logic circuit, processor, microprocessor, Central Processing Unit (CPU), Graphics Processing Unit (GPU), Digital Signal Processor (DSP), Field Programmable Gate Array (FPGA), integrated circuit, Application Specific Integrated Circuit (ASIC), etc., or any combination thereof. Any other kind of implementation of the respective functions, which will be described below in further detail, may also be understood as a processor, controller, or logic circuit. It is understood that any two (or more) of the processors, controllers, or logic circuits detailed herein may be realized as a single entity with equivalent functionality or the like, and conversely that any single processor, controller, or logic circuit detailed herein may be realized as two (or more) separate entities with equivalent functionality or the like.

As used herein, "memory" is understood as a computer-readable medium (e.g., a non-transitory computer-readable medium) in which data or information can be stored for retrieval. References to "memory" included herein may thus be understood as referring to volatile or non-volatile memory, including random access memory (RAM), read-only memory (ROM), flash memory, solid-state storage, magnetic tape, hard disk drive, optical drive, 3D XPoint™, among others, or any combination thereof. Registers, shift registers, processor registers, data buffers, among others, are also embraced herein by the term memory. The term "software" refers to any type of executable instruction, including firmware.

Unless explicitly specified, the term "transmit" encompasses both direct (point-to-point) and indirect transmission (via one or more intermediary points). Similarly, the term "receive" encompasses both direct and indirect reception. Furthermore, the terms "transmit," "receive," "communicate," and other similar terms encompass both physical transmission (e.g., the transmission of radio signals) and logical transmission (e.g., the transmission of digital data over a logical software-level connection). For example, a processor or controller may transmit or receive data over a software-level connection with another processor or controller in the form of radio signals, where the physical transmission and reception is handled by radio-layer components such as RF transceivers and antennas, and the logical transmission and reception over the software-level connection is performed by the processors or controllers. The term "communicate" encompasses one or both of transmitting and receiving, i.e., unidirectional or bidirectional communication in one or both of the incoming and outgoing directions. The term "calculate" encompasses both 'direct' calculations via a mathematical expression/formula/relationship and 'indirect' calculations via lookup or hash tables and other array indexing or searching operations.

If a vehicle is involved in a collision, emergency responders may receive basic information regarding the vehicle and occupants. For example, the emergency responders may receive information indicating a number of occupants, a make or model of the vehicle, a location of the collision, odometry, or some combination thereof.

In Europe, modern vehicles may include an eCall system. Messages transmitted using the eCall system may indicate a location of the collision a severity of an impact of the collision, or other information related to the vehicle. In addition, a voice call may be initiated with the vehicle to try and communicate with the occupants of the vehicle. However, if the occupants are unconscious or unable to speak, the eCall system may not establish communication with the occupants. In addition, current information provided using the eCall system may only indicate a status of the vehicle and not information related to the occupants. Emergency responders may operate more effectively if they are provided information related to a state and health of the occupants of the vehicle.

Some aspects described in the present disclosure may provide information related to a state and health of the occupants of the vehicle after a collision. The vehicle may include a driver monitoring system (DMS). The DMS may include sensors that monitor the state, a position, a pose, or some other combination of the occupants prior to, during, and after the collision. The DMS may provide sensor data to a response center to assist the emergency responders in preparing to respond to the collision. The sensor data may include kinematic information, medical information, or some combination thereof of the occupants of the vehicle. In addition, the sensor data may be compared to data corresponding to previous accidents to determine (e.g., estimate) a severity of the collision. The DMS may also determine (e.g., estimate) a severity of injuries of the occupants.

The DMS may include a camera to monitor for wounds, trauma, or other external injuries of the occupants. For example, the DMS may determine whether a color of clothes of the occupants is changing (e.g., getting darker or becoming red) due to blood from a wound using the camera. As another example, the DMS may detect bone fractures in extremities of the occupants (e.g., arms, legs, fingers, head, or some combination thereof using the camera. Further, the DMS may include a medical sensor that is configured to detect a medical state of the occupants. For example, the DMS may include a heart rate sensor, an infrared sensor, an acoustic sensor, a respiratory sensor, or some combination thereof. The DMS may detect internal injuries of the occupants based on the detected medical state. For example, if a heart rate of the occupant decreases, the DMS may determine the occupant may include an internal injury. As another example, the DMS may determine whether the occupant is unconscious (e.g., not currently moving but is still breathing or has a heart rate). The DMS may also determine a psychological state of the occupant based on facial expressions of the occupant or acoustic data.

The DMS may include a memory having computer-readable instructions stored thereon. The DMS may also include a processor operatively coupled to the memory. The processor may be configured to read and execute the computer-readable instructions to perform or control performance of operations. The operations may include receive, prior to the collision involving the vehicle, first sensor data representative of a first feature of an internal environment of the vehicle. The operations may also include determine the collision has occurred. In addition, the operations may include automatically instruct, based on the collision, a sensor to generate second sensor data. The second sensor data may be representative of a second feature of the internal environment of the vehicle. Further, the operations may include receive the second sensor data from the sensor. The operations may include compare the first sensor data and the second sensor data to accident data corresponding to previous accidents. The accident data may include a diagnosed injury, an accident severity, or some combination thereof of each of the previous accidents. The operations may also include determine a severity of the collision based on the comparison.

In addition, the operations may include identify, prior to the collision, a pose of the occupant of the vehicle. The operations may also include compare the pose to known risk poses. Further, the operations may include determine a likelihood and a severity of an injury of the occupant based on the comparison. Responsive to the likelihood and the severity of the injury of the occupant exceeding a threshold value, the operations may include provide a message to the occupant indicating the occupant should change their pose.

The DMS described in the present disclosure may provide, to emergency responders, detailed information regarding estimated injuries of occupants of the vehicle prior to the emergency responders arrive. The DMS may also provide a combination of driver monitoring systems with emergency response support. In addition, a cloud-based database may be utilized by the DMS to improve in-vehicle safety.

These and other aspects of the present disclosure will be explained with reference to the accompanying figures. It is to be understood that the figures are diagrammatic and schematic representations of such example aspects, and are not limiting, nor are they necessarily drawn to scale. In the figures, features with like numbers indicate like structure and function unless described otherwise.

FIG. 1 illustrates a block diagram of an exemplary operational environment 100 of a vehicle 102 that includes a DMS 104 to estimate a severity of an injury using in-vehicle perception, in accordance with at least one aspect described in the present disclosure. The operational environment 100 may also include a response center 114 (e.g., an emergency response center).

The DMS 104 may include a memory 106, a processor 108, a transceiver 110, a first sensor 112, a second sensor 120, or some combination thereof. The DMS 104 may be communicatively coupled to the response center 114. For example, the transceiver 110 may be configured to wirelessly couple the DMS 104 and the response center 114 via a wireless link 111. In some aspects, the first sensor 112 and the second sensor 120 may be combined into a single sensor. The first sensor 112 and the second sensor 120 may include a camera, a light detection and ranging sensor, an acoustic sensor, an accelerometer, a red green blue-depth (RGB-D) sensor a heart rate sensor, an infrared sensor, a respiratory sensor, or some combination thereof. The first sensor 112 and the second sensor 120 may provide a multi-modal sensor setup to capture sensor data representative of an internal environment of the vehicle 102 (e.g., the interior of the vehicle).

The memory 106 may include an accident database 116, a pose database 118, or some combination thereof. Additionally or alternatively, the response center 114 may include the accident database 116. The accident database 116 may include accident data representative of previous accidents involving other vehicles. The accident data may include a diagnosed injury and an accident severity of the previous accidents The pose database 118 may include data representative of known risk poses of occupants of the vehicle 102 (not illustrated in FIG. 1). Known risk poses may include poses of the occupants of the vehicle 102 that exceed a threshold value.

The first sensor 112 may use a multi-modal sensor setup to capture first sensor data. The first sensor data may be representative of a first feature of an internal environment of the vehicle 102. The first feature may correspond to at least one of a pose or a position of an occupant of the vehicle prior to and during the collision. For example, the first feature may indicate features of body parts of the occupants (e.g., head, arms, hands, legs, feet, torso, or some combination thereof of the occupant). Additionally or alternatively, the first feature may correspond to an interior surface of the internal volume. In addition, the first sensor data may include kinematic information of the occupant of the vehicle. Further, the kinematic information may indicate a direction of a movement of the occupant relative to the vehicle during the collision, a velocity of the movement of the occupant during the collision, a pose of the occupant prior to the collision, a pose of the occupant during the collision, or a deformation of an interior surface of the vehicle during the collision, or some combination thereof. The DMS 104 may store the first sensor data in a memory 106.

The processor 108 may receive, prior to a collision involving the vehicle 102, the first sensor data. The processor 108 may identify, prior to the collision, a pose of an occupant of the vehicle based on the first feature. The processor 108 may also receive the pose database 118 from the memory 118. The processor 108 may compare the pose of the occupant to known risk poses within the pose database 118. The processor 108 may determine a likelihood and severity of an injury (e.g., an estimated likelihood and severity) of the occupant based on the comparison. In addition, the processor 108 may, responsive to the likelihood and severity of the injury of the occupant exceeding a threshold value, provide a message to the occupant indicating the occupant should change their pose. For example, the vehicle 102 may include internal speakers (not illustrated in FIG. 1) and the processor 108 may provide an audio warning to the occupant via the speakers.

The processor 108 may determine a collision has occurred (e.g., may determine the vehicle 102 has been involved in a collision or an accident). The processer 108 may automatically instruct, based on the collision occurring, the first sensor 112, the second sensor 120, or some combination thereof to generate second sensor data. The processor 108 may instruct the first sensor 112, the second sensor 120, or some combination thereof to generate the second sensor data.

The second sensor 120 may generate the second sensor data. The second sensor data may be representative of a second feature of the internal environment of the vehicle. The second feature may correspond to a state of the occupant of the vehicle after the collision. The second sensor data may include medical information of the occupant of the vehicle 102. For example, the medical information may include a heart rate of the occupant, a body temperature of the occupant, a presence of external bleeding of the occupant, a consciousness state of the occupant, a facial expression of the occupant, a state of a skeletal structure of the occupant, a respiratory rate of the occupant, or some combination thereof. The DMS 104 may store the second sensor data in the memory 106.

The processor 108 may receive the second sensor data from the second sensor 120. The processor 108 may also receive the accident database 116. The processor 108 may receive the accident database 116 from the memory 106 or from the response center 114 (e.g., via the transceiver 110 and the wireless link 111). The processor 108 may compare the first sensor data and the second sensor data to the accident data within the accident database 116. In addition, the processor 108 may determine a severity of the collision based on the comparison. The processor 108 may determine a severity of an injury to a part or the entire body of the occupant based on the first sensor data, the second sensor data, or some combination thereof. The processor 108 may generate a severity message. The severity message may be representative of the severity of the collision, the first sensor data, the second sensor data, a state of an occupant of the vehicle, or some combination thereof.

The transceiver 110 may continuously transmit the severity message to the response center 114. For example, the transceiver 110 may continuously transmit the severity message to the response center 114 to provide a current status of the occupant of the vehicle. If the current status of the occupant changes (e.g., the occupant wakes up or a heart rate of the occupant changes), the processor 108 may update the severity message and the transceiver 110 may continuously transmit the updated severity message.

Figure 2:
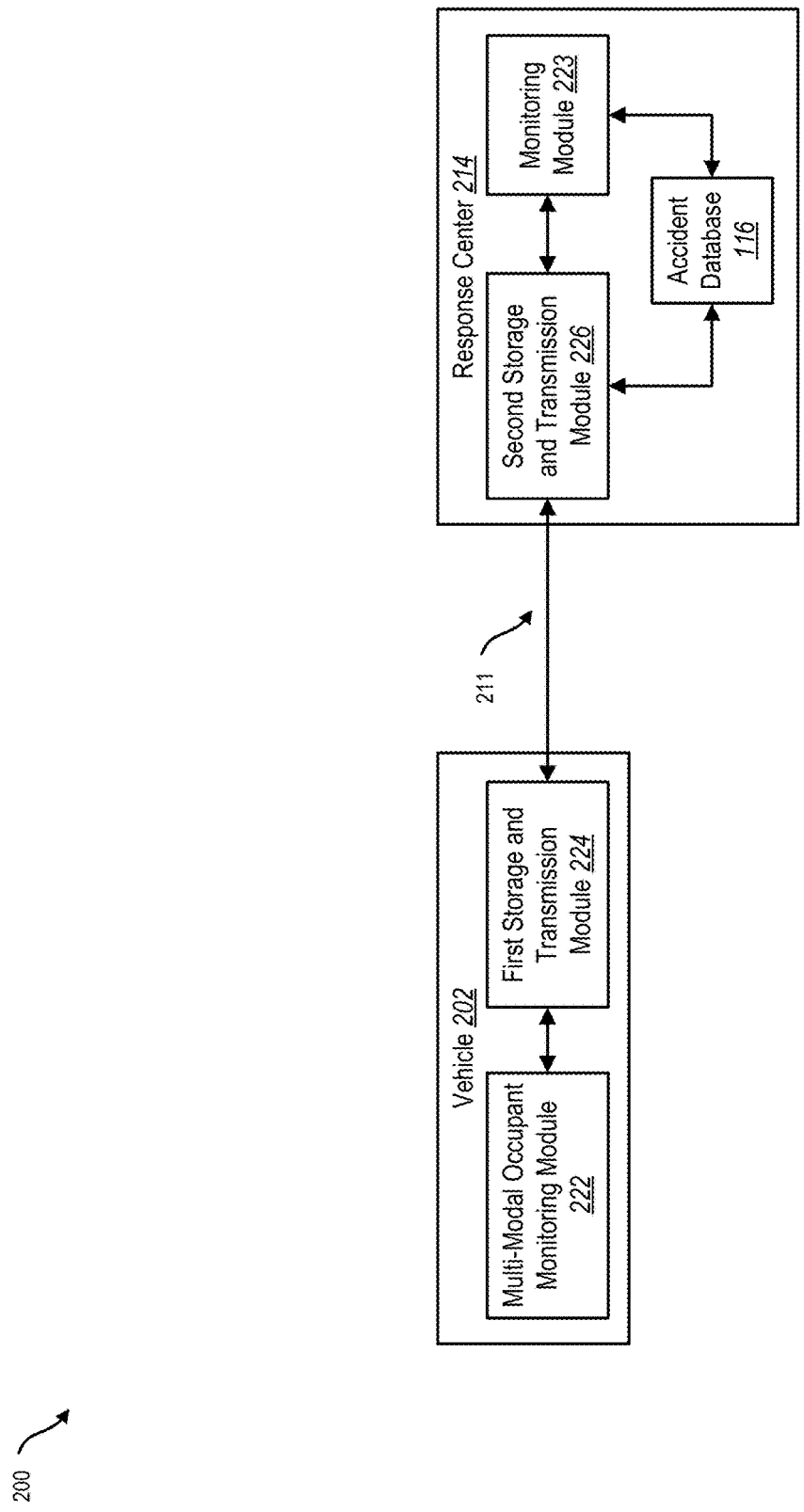
FIG. 2 illustrates a block diagram of another exemplary operational environment of a vehicle to estimate the severity of an injury using in-vehicle perception.

FIG. 2 illustrates a block diagram of another exemplary operational environment 200 of a vehicle 202 to estimate the severity of an injury using in-vehicle perception, in accordance with at least one aspect described in the present disclosure. The operational environment 200 may include the vehicle 202 and a response center 214 (e.g., an emergency response center).

The vehicle 202 may include a multi-modal occupant monitoring module (MOMM) 222 and a first storage and transmission module 224. The MOMM 222 and the first storage and transmission module 224 may correspond to the DMS 104 of FIG. 1. For example, the MOMM 222 may correspond to the first sensor 112, the second sensor 120, and the processor 108 and the first storage and transmission module 224 may correspond to the memory 106 and the transceiver 110 of FIG. 1.

The MOMM 222 may include code and routines configured to enable a computing device to perform one or more operations with respect to monitoring occupants of the vehicle 202 (not illustrated in FIG. 2). Additionally or alternatively, the MOMM 222 may be implemented using hardware including a processor, a microprocessor (e.g., to perform or control performance of one or more operations), a field-programmable gate array (FPGA), or an application-specific integrated circuit (ASIC). In some other instances, the MOMM 222 may be implemented using a combination of hardware and software. In the present disclosure, operations described as being performed by the MOMM 222 may include operations that the MOMM 222 may direct a corresponding system to perform.

The first storage and transmission module 224 may include code and routines configured to enable a computing device to perform one or more operations with respect to monitoring occupants of the vehicle 202 (not illustrated in FIG. 2). Additionally or alternatively, the first storage and transmission module 224 may be implemented using hardware including a processor, a microprocessor (e.g., to perform or control performance of one or more operations), a FPGA, or an ASIC. In some other instances, the first storage and transmission module 224 may be implemented using a combination of hardware and software. In the present disclosure, operations described as being performed by the first storage and transmission module 224 may include operations that the first storage and transmission module 224 may direct a corresponding system to perform.

The response center 214 may include a second storage and transmission module 226, a monitoring module 223, and the accident database 116. The response center 214 may correspond to the response center 114 of FIG. 1. The first storage and transmission module 224 and the second storage and transmission module 226 may be communicatively coupled via a wireless link 211. The MOMM 222 may provide a multi-modal sensor setup to capture sensor data representative of an internal environment of the vehicle 202.

The second storage and transmission module 226 may include code and routines configured to enable a computing device to perform one or more operations with respect to monitoring occupants of the vehicle 202 (not illustrated in FIG. 2). Additionally or alternatively, the second storage and transmission module 226 may be implemented using hardware including a processor, a microprocessor (e.g., to perform or control performance of one or more operations), a FPGA, or an ASIC. In some other instances, the second storage and transmission module 226 may be implemented using a combination of hardware and software. In the present disclosure, operations described as being performed by the second storage and transmission module 226 may include operations that the second storage and transmission module 226 may direct a corresponding system to perform.

The monitoring module 223 may include code and routines configured to enable a computing device to perform one or more operations with respect to monitoring occupants of the vehicle 202 (not illustrated in FIG. 2). Additionally or alternatively, the monitoring module 223 may be implemented using hardware including a processor, a microprocessor (e.g., to perform or control performance of one or more operations), a FPGA, or an ASIC. In some other instances, the monitoring module 223 may be implemented using a combination of hardware and software. In the present disclosure, operations described as being performed by the monitoring module 223 may include operations that the monitoring module 223 may direct a corresponding system to perform.

The MOMM 222 may receive, prior to a collision involving the vehicle 202, the first sensor data representative of the first feature. The MOMM 222 may determine a collision involving the vehicle 202 has occurred. The MOMM 222 may automatically instruct, based on the collision occurring, a sensor to generate second sensor data. The MOMM 222 may receive the accident database 116 from the response center 214 via the first storage and transmission module 224 and the second storage and transmission module 226. The MOMM 222 may compare the first sensor data and the second sensor data to the accident data within the accident database 116. In addition, the MOMM 222 may determine a severity of the collision based on the comparison. The MOMM 220 may also generate the severity message.

The first storage and transmission module 224 may continuously transmit the severity message to the response center 214. For example, the first storage and transmission module 224 may continuously transmit the severity message to the response center 214 to provide a current status of the occupant of the vehicle. If the current status of the occupant changes (e.g., the occupant wakes up or a heart rate of the occupant changes), the MOMM 222 may update the severity message and the first storage and transmission module 224 may continuously transmit the updated severity message.

Alternatively, the MOMM 22 may provide the first sensor data and the second sensor data to the response center 214 via the first storage and transmission module 224. The monitoring module 223 may receive the first sensor data and the second sensor data via the second storage and transmission module 226. The monitoring module 223 may compare the first sensor data and the second sensor data to the accident data within the accident database 116. The monitoring module 223 may determine a severity of the collision based on the comparison.

The first storage and transmission module 224, responsive to the collision occurring, may continuously transmit the first sensor data and the second sensor data to the response center 214. The monitoring module 223 may determine a current status of the occupant of the vehicle. If the current status of the occupant changes (e.g., the occupant wakes up or a heart rate of the occupant changes), the monitoring module 223 may update the severity of the collision.

Figure 3:
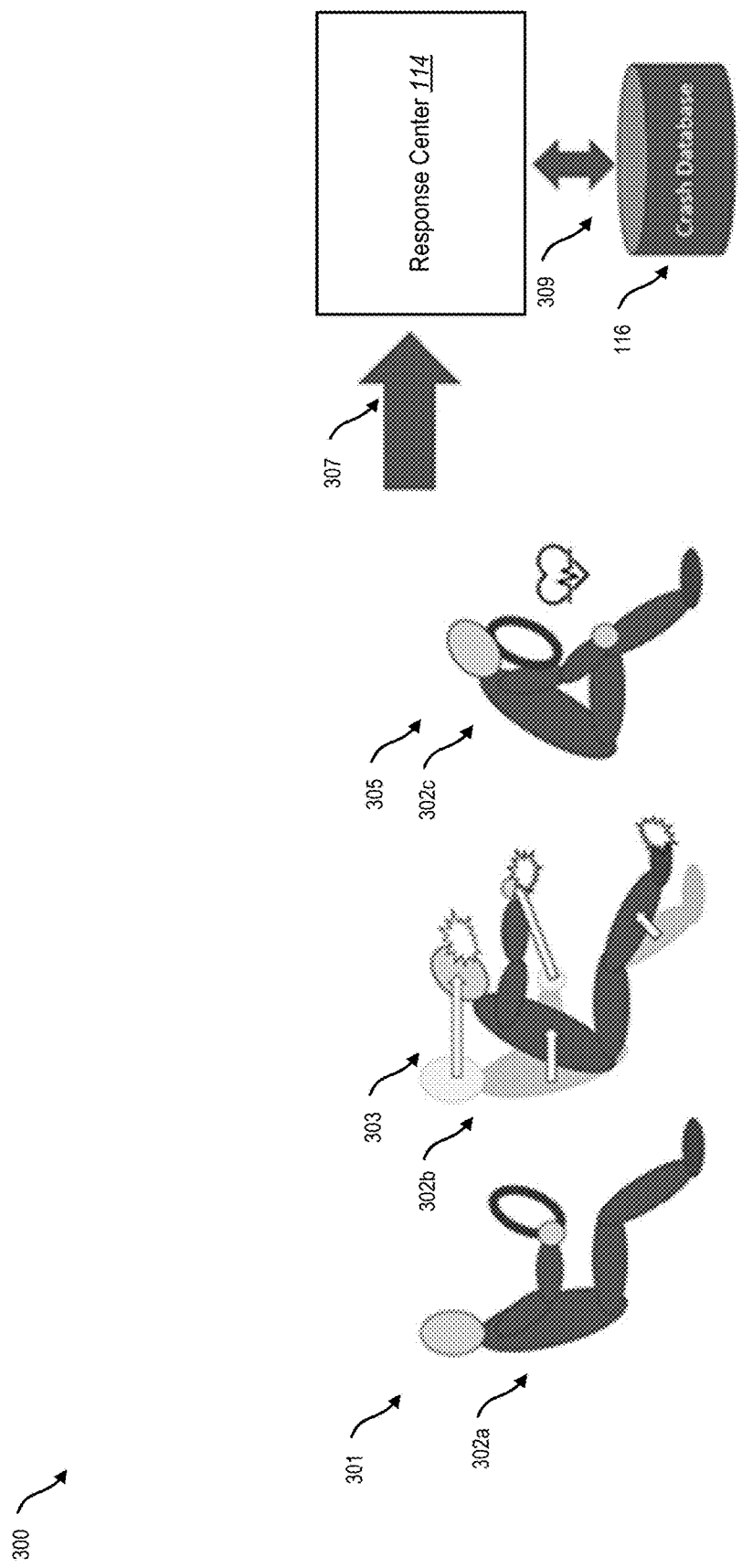
FIG. 3 illustrates a flowchart of an exemplary method to estimate the severity of an injury using in-vehicle perception.

FIG. 3 illustrates a flowchart of an exemplary method 300 to estimate the severity of an injury using in-vehicle perception, in accordance with at least one aspect described in the present disclosure. The method 300 may be performed by any suitable system, apparatus, or device with respect to estimating the severity of an injury of an occupant of the vehicle 102 using in-vehicle perception. For example, the DMS 104, the processor 108, the MOMM 222, the first and second storage and transmission modules 324 326, the response centers 114 214, the monitoring module 223, or some combination thereof of FIGS. 1 and 2 may perform or direct performance of one or more of the operations associated with the method 300. The method 300 is described in relation to FIG. 3 as being performed by the DMS 104 and the response center 114 for example purposes. The method 300 may include one or more operations 301, 303, 305, 307, and 309. Although illustrated with discrete operations, the operations associated with the method 300 may be divided into additional operations, combined into fewer operations, or eliminated, depending on the particular implementation.

At operation 301, prior to the collision, the DMS 104 may generate and store the first sensor data. The first sensor data may be representative of the first feature of the internal environment of the vehicle prior to the collision. The first feature may correspond to a pose or a position of an occupant of the vehicle, an interior surface of the internal volume, or some combination thereof prior to the collision.

At operation 303, during the collision, the DMS 104 may continue generating the first sensor data. The first sensor data may be representative of the first feature of the internal environment of the vehicle during the collision. The first feature may correspond to a pose or a position of an occupant of the vehicle, an interior surface of the internal volume, or some combination thereof during the collision. The DMS 104 may store the first sensor data in memory.

At operation 305, after the collision, the DMS 104 may generate and store the second sensor data. The second sensor data may be representative of the second feature of the internal environment of the vehicle. The second feature may correspond to a state of the occupant of the vehicle, medical information, or some combination thereof after the collision. The DMS 104 may store the second sensor data in memory. In addition, the DMS 104 may generate the severity message.

At operation 307, after the collision, the DMS 104 may transmit the severity message to the response center 114. For example, the DMS 104 may transmit the severity message indicating a pose, a movement, a deformation, health data, or any other appropriate information to the response center 114. At operation 309, after the collision, the response center 114 may compare the first sensor data and the second sensor data to the accident data in the accident database 116. In addition, the response center 114 may identify similar accidents based on the comparison.

Figure 4:
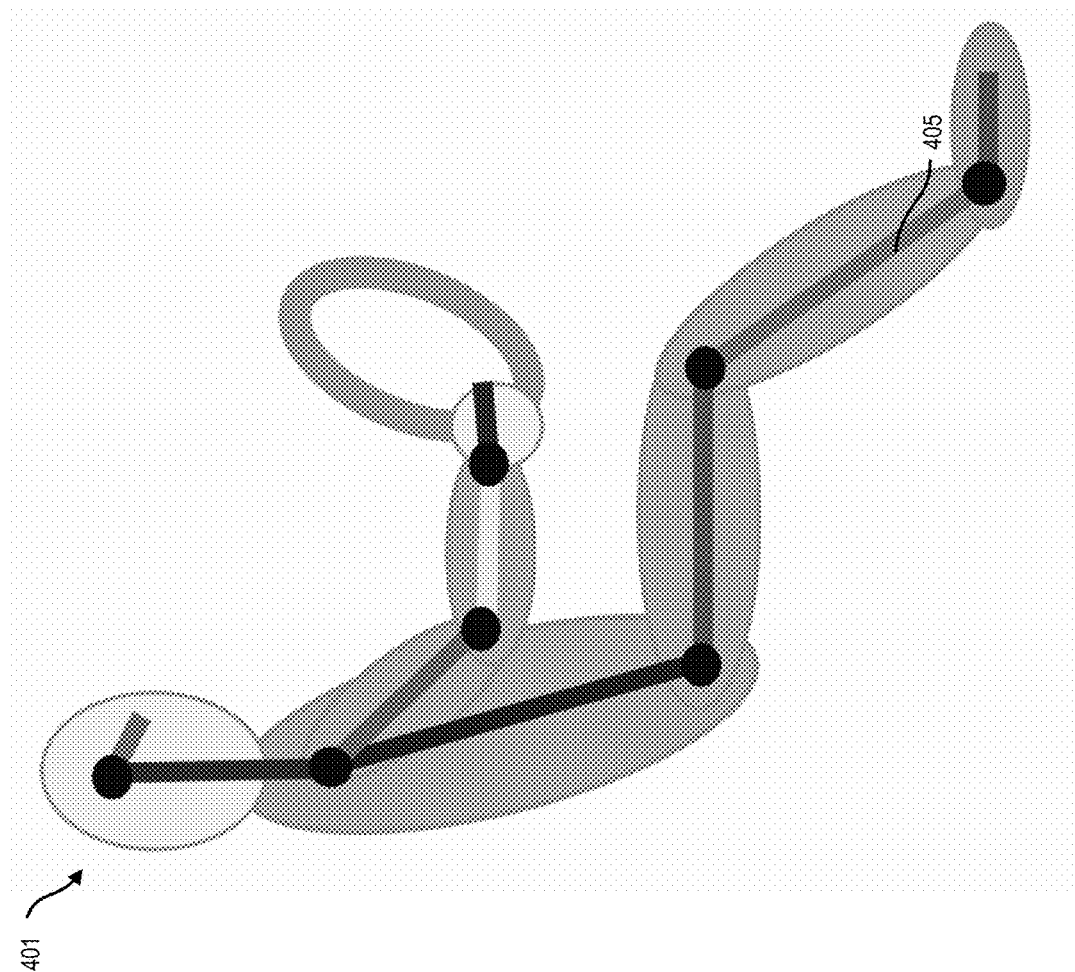
FIG. 4 illustrates an exemplary detected pose of an occupant of a vehicle.

FIG. 4 illustrates an exemplary detected pose 405 of an occupant 401 of a vehicle, in accordance with at least one aspect described in the present disclosure. The detected pose 405 may include a virtual representation of features of the body of the occupant 401 within the internal environment of the vehicle. The detected pose 405 may be generated based on the first sensor data. As illustrated in FIG. 4, the detected pose 405 may represent extremities and other portions of the bodies of the occupant 401.

Figure 5:
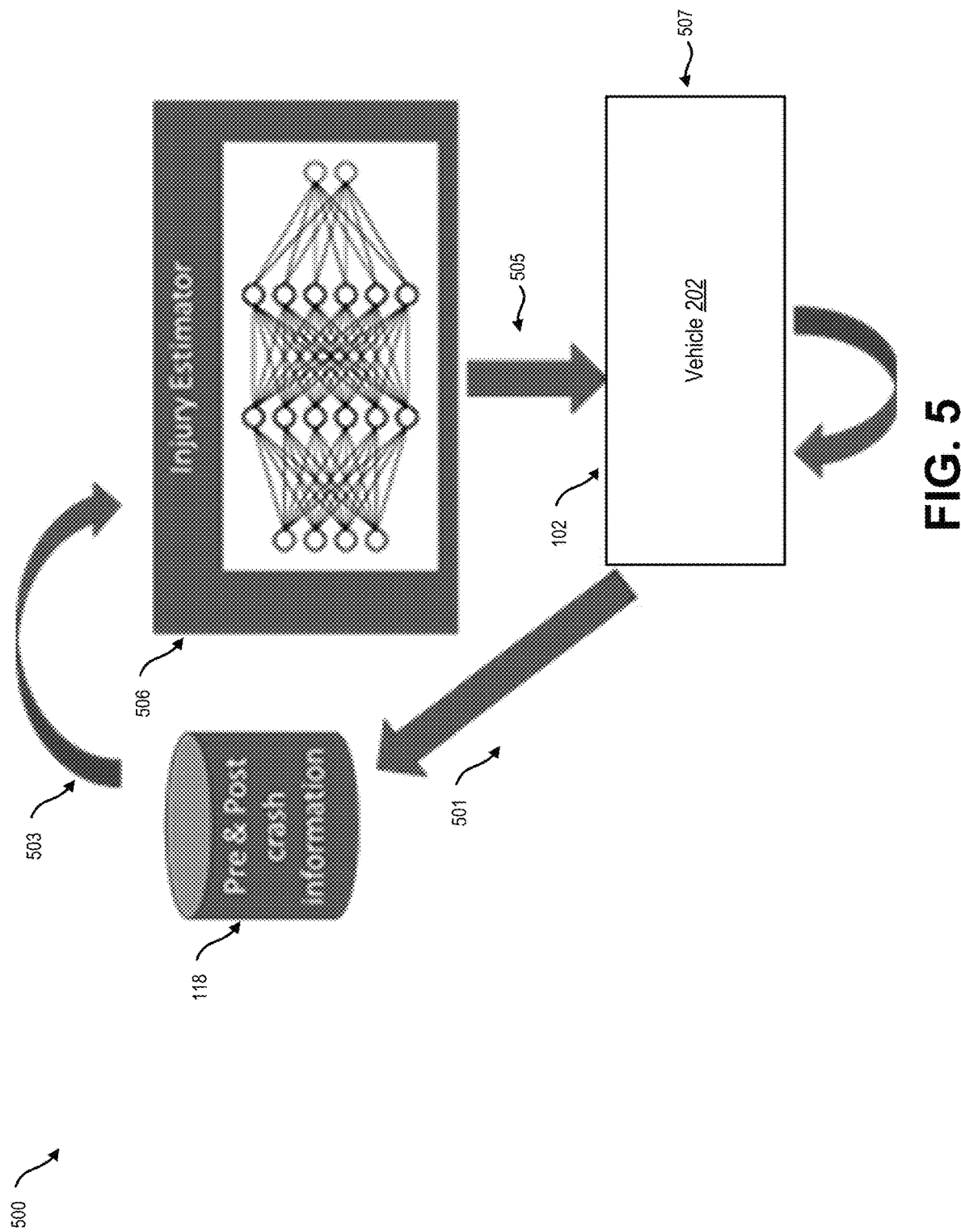
FIG. 5 illustrates a flowchart to train and deploy an injury estimator using in-vehicle perception, all according to at least one aspect described in the present disclosure.

FIG. 5 illustrates a flowchart of an exemplary method 500 to train and deploy an injury estimator 506 using in-vehicle perception, in accordance with at least one aspect described in the present disclosure. The method 500 may be performed by any suitable system, apparatus, or device with respect to estimating the severity of an injury of an occupant of the vehicle 102 using in-vehicle perception. For example, the DMS 104, the processor 108, the MOMM 222, the first and second storage and transmission modules 324 326, the response centers 114 214, the monitoring module 223, or some combination thereof of FIGS. 1 and 2 may perform or direct performance of one or more of the operations associated with the method 500. The method 500 is described in relation to FIG. 5 as being performed by the DMS 104 for example purposes. The method 500 may include one or more operations 501, 503, 505, and 507. Although illustrated with discrete operations, the operations associated with the method 500 may be divided into additional operations, combined into fewer operations, or eliminated, depending on the particular implementation. The method 500 may permit the DMS 104 to estimate a severity of a potential injury based on a current pose of an occupant of the vehicle.

At operation 501, the DMS 104 may upload known poses of an occupant to the pose database 118. The known poses may be obtained using the first sensor 112 or from another database. At operation 503, the DMS 104 may train the injury estimator 506 using machine learning algorithms and the pose database 118. For example, the DMS 104 may train the injury estimator 506 using a neural network machine learning algorithm. At operation 505, the DMS 104 may deploy the injury estimator 506 in the vehicle 102.

At operation 507, the DMS 104 may monitor a current pose of the occupant and warn the occupant if the current pose is dangerous. The DMS 104 may identify, prior to the collision, the pose of the occupant of the vehicle. The DMS 104 may also compare the pose to the known risk poses within the pose database 118. For example, the DMS 104 may use the injury estimator 506 to identify known poses within the pose database 118 that are similar to the current pose of the occupant.

The DMS 104 may determine a likelihood and severity of an injury of the occupant based on the comparison. The DMS 104 may determine whether the pose of the occupant exceeds the threshold value. Responsive to the likelihood and severity of the injury of the occupant exceeding the threshold value, the DMS 104 may provide a message to the occupant indicating the occupant should change their pose. For example, the vehicle 102 may include internal speakers and the DMS 104 may provide an audio warning to the occupant via the speakers.

In some technologies, if a vehicle is involved in a collision, emergency responders may only initially receive basic information regarding the vehicle and occupants. For example, the emergency responders may receive information indicating a number of occupants, a make or model of the vehicle, a location of the collision, odometry, or some combination thereof.

In Europe, modern vehicles may include an eCall system. Messages and information transmitted using the eCall system may indicate a location of the collision, a severity of an impact of the collision, or other information related to the vehicle. In addition, a voice call may be initiated with the vehicle to try and communicate with the occupants of the vehicle. However, if the occupants are unconscious or unable to speak, the eCall system may not establish communication with the occupants. In addition, current information provided using the eCall system may only indicate a status of the vehicle and not information related to the occupants. Emergency responders may operate more effectively if they are provided information related to a state and health of the occupants of the vehicle.

The DMS described in the present disclosure may include three modules. The DMS may include a MOMM, a data storage and transmission module, and a monitoring module. The MOMM may include a multi-modal sensor setup to capture sensor data. The MOMM may include a camera, an RGB-D sensor, a LIDAR sensor, or some combination thereof. The MOMM may also include a heart rate sensor, an infrared sensor, an acoustic sensor, or some combination thereof. The different sensors of the MOMM might be of different importance prior to, during, or after a collision.

Prior to and during the collision, focus may be on analyzing an impact of the collision. The impact of the collision may be used to derive an injury severity, movement of a body of the occupant (e.g., limbs, extremities, the head, etc.) over time, or some combination thereof. The movement of the body of the occupant may include abrupt velocity changes due to contacting hard surfaces (e.g. when contacting surfaces such as the dashboard or the steering wheel). The DMS may detect a pose of the occupant using the sensor data. Additionally, the DMS may determine a deformation of an interior surface of the vehicle. The DMS may also determine a number and a position of triggered airbags in the vehicle, the measured acceleration values of the accelerometers within the vehicle, or some combination thereof.

The data storage and transmission module may receive the sensor data from the MOMM and may store the sensor data. In case of a collision, the data storage and transmission module may transmit the relevant sensor data to a response center. For example, the data storage and transmission module may transmit the sensor data obtained prior to the collision (e.g., a few seconds prior to the impact) and the sensor data obtained during the collision. The data storage and transmission module may use an eCall communication channel. The data storage and transmission module may continuously transmit the sensor data after the collision to provide emergency responders with a live view on a health state of the occupant. The sensor data may include a live video stream of the internal environment of the vehicle.

The monitoring module may include a database of previous accidents (e.g., an accident database) and diagnosed injuries and severities of the collisions. If a collision is reported, the DMS may use an algorithm to compare the sensor data (e.g., the impact analysis and health data) with the accident database. The monitoring module may estimate an injury severity of the occupant that may be forwarded to the emergency responders or even a hospital. The sensor data may be added to the accident database to further increase the amount of information in the accident database.

The DMS may include a memory having computer-readable instructions stored thereon. The DMS may include a processor operatively coupled to the memory. The processor may be configured to read and execute the computer-readable instructions to perform or control performance of operations. The DMS may receive, prior to the collision involving the vehicle, the first sensor data. The first sensor data may be representative of the first feature of the internal environment of the vehicle. The first feature may correspond to the pose or the position of the occupant of the vehicle prior to and during the collision. The first feature may indicate tracking of all body parts of the occupant (e.g., the head, the arms, the legs, the torso, the hands, the feet, of the occupant) prior to, during, and after the collision. For example, the first feature may indicate that the head of the occupant, during the collision, contacted an airbag and then moves backwards and contacted a headrest that is positioned too low.

The first feature may correspond to the interior surface of the internal volume. The first sensor data may include kinematic information of the occupant of the vehicle. For example, the first sensor data may include kinematic information of the occupant relative to the vehicle. The kinematic information may indicate at least one of a direction of a movement of the occupant relative to the vehicle during the collision, a velocity of the movement of the occupant during the collision, the pose of the occupant prior to the collision, the pose of the occupant during the collision, a deformation of an interior surface of the vehicle during the collision, or some combination thereof. The DMS 104 may store the first sensor data in a memory. The DMS may determine that the collision has occurred. The DMS may also receive, during the collision, the first sensor data.

The DMS may use available sensor data about body movements and health indicators of the occupant. Examples of the body movements may include the direction and speed of the human extremities when contacting the interior surface of the vehicle. The DMS may determine materials specific to the vehicle to determine a rate of impact of the occupant with the interior surface. For example, a head impact with the airbag may be determined to be less severe than an impact with the dashboard.

Deformations of the extremities of the occupant may be determined according to possible ranges of movement given by the human anatomy and the ability of the body to compensate. For example, the DMS may determine the occupant includes a broken wrist, if a hand of the occupant was bent too much in a specific direction. Health indicators like heart rate or body temperature may be rated between normal and abnormal. As all values may be probabilistic, the DMS may use an AI-based algorithm to determine the injury estimation. A model of the musculoskeletal system (e.g. in which directions may a human arm and corresponding joints move) may be used to estimate an injury. For example, during the collision an arm of the occupant may contact the dashboard and may be forced into a position that causes a fracture to occur.

The DMS may automatically instruct, based on the collision occurring, a sensor to generate second sensor data. The second sensor data may be representative of a second feature of the internal environment of the vehicle. The sensor may include a first sensor or a second sensor. In some aspects, the first sensor data may be received from the first sensor. The first sensor and the second sensor may include a camera, a light detection and ranging sensor, an acoustic sensor, an accelerometer, an RGB-D sensor, a heart rate sensor, an infrared sensor, a respiratory sensor, or some combination thereof.

The second feature may correspond to a state of the occupant of the vehicle after the collision. The second feature may indicate (e.g., the second sensor data may include) medical information related to the occupant. The medical information may include a heart rate of the occupant, a body temperature of the occupant, a presence of external bleeding of the occupant, a consciousness state of the occupant, a facial expression of the occupant, a state of a skeletal structure of the occupant, a respiratory rate of the occupant, or some combination thereof.

The DMS may receive and store the second sensor data in the memory. The DMS may determine a severity of the collision based on the first sensor data and the second sensor data. The DMS may compare the first sensor data and the second sensor data to the accident database. The accident database may include accident data corresponding to previous accidents. The accident data may include a diagnosed injury, an accident severity, or some combination thereof of the previous accidents. The DMS may identify a previous accident that is similar to the collision based on the comparison. The DMS may determine the severity of the collision based on the identified previous accident.

The DMS may determine a deformity of the interior surface of the vehicle based on a difference between the first feature prior to the collision and the first feature during the collision. The DMS may determine the severity of the collision based on the deformity of the interior surface.

The DMS may continuously transmit, responsive to determining the collision has occurred, a severity message to the response center The severity message may be representative of the severity of the collision, the first sensor data, the second sensor data, a state of an occupant of the vehicle, or some combination thereof. The severity message may also indicate the estimated injury of the occupant based on the diagnosed injury of the identified previous accident.

The DMS may also use a pose database, the accident database, or some combination thereof to train an injury estimator to improve occupant safety in general. Detailed information about the pose of the occupant prior to the collision could be used to determine a likelihood and severity of an injury of a collision were to occur such that warnings may be provided to the occupant. For example, the warnings may instruct the occupant to not put their feet on the dashboard. Therefore, the DMS may use the sensor data to train an injury predictor to estimate the likelihood of a severe injury given the current pose of the passengers in the vehicle.

The first and second sensor data may be stored in a database together with information about the severity of the injuries. The stored information may be used to train the injury estimator. The injury estimator may be deployed in the vehicle to monitor and determine when unsafe poses are occurring. The first sensor data may be continuously provided to the injury estimator, which may determine if a risk of injury due to a current pose of the occupant exceeds a threshold value. If the risk of injury due to the current pose exceeds the threshold value (e.g., if the pose causes a high likelihood that a fatal consequence may occur if a collision were to occur), the DMS may provide a warning to the occupant.

The DMS may identify, prior to the collision, the pose of the occupant of the vehicle. The DMS may also compare the pose to known risk poses within the pose database. In addition, the DMS may determine the likelihood and severity of an injury of the occupant based on the comparison. Further, responsive to the likelihood and severity of the injury of the occupant exceeding the threshold value, the DMS may provide a message to the occupant indicating the occupant should change their pose.

The sensor data may be used to estimate responsibilities, liabilities, or some combination thereof of drivers involved in the collision. For example, if the vehicle is an automated vehicle, the sensor data may be used to determine if the automated vehicle is liable for the accident. In addition, the sensor data may be used by vehicle manufacturers to determine interior surfaces of the vehicle that should be modified to reduce the likelihood of severe injuries occurring (e.g., due to sharp edges that only occur due to the collision).

A non-transitory computer-readable medium may include computer-readable instructions stored thereon that are executable by a processor to perform or control performance of operations. The operations may include receive, prior to a collision involving a vehicle, first sensor data. The first sensor data may be representative of a first feature of an internal environment of a vehicle. The operations may also include determine the collision has occurred. In addition, the operations may include automatically instruct, based on the collision, a sensor to generate second sensor data. The second sensor data may be representative of a second feature of the internal environment of the vehicle. Further, the operations may include receive the second sensor data from the sensor. The operations may include determine a severity of the collision based on the first sensor data and the second sensor data.

The operations may also include including continuously transmit, responsive to determining the collision has occurred, a severity message to an emergency response center. The severity message may be representative of at least one of the severity of the collision, the first sensor data, the second sensor data, or a state of an occupant of the vehicle.

The operation determine the severity of the collision may include compare the first sensor data and the second sensor data to an accident database. The accident database may include accident data corresponding to previous accidents. The accident data may include a diagnosed injury and an accident severity of each of the previous accidents. The operation determine the severity of the collision may also include identify a previous accident that is similar to the collision based on the comparison. The severity of the collision may be determined based on the identified previous accident. The severity message may further indicate an estimated injury of the occupant based on the diagnosed injury of the identified previous accident.

The operations may include receive, during the collision, the first sensor data. The first feature may correspond to at least one of a pose or a position of an occupant of the vehicle prior to and during the collision. The second feature may correspond to a state of the occupant of the vehicle after the collision. The first feature may correspond to an interior surface of the internal volume. The operation determine the severity of the collision may include determine a deformity of the interior surface based on a difference between the first feature prior to the collision and the first feature during the collision. The severity of the collision may be determined based on the deformity of the interior surface.

The first sensor data may include kinematic information of the occupant of the vehicle. The second sensor data may include medical information of the occupant. The kinematic information may indicate at least one of a direction of a movement of the occupant relative to the vehicle during the collision, a velocity of the movement of the occupant during the collision, a pose of the occupant prior to the collision, a pose of the occupant during the collision, or a deformation of an interior surface of the vehicle during the collision. The medical information may include at least one of a heart rate of the occupant, a body temperature of the occupant, a presence of external bleeding of the occupant, a consciousness state of the occupant, a facial expression of the occupant, a state of a skeletal structure of the occupant, or a respiratory rate of the occupant.

The sensor may include at least one of a camera, a light detection and ranging sensor, an acoustic sensor, an accelerometer, an RGB-D sensor a heart rate sensor, an infrared sensor, or a respiratory sensor.

The operations may also include identify, prior to the collision, a pose of an occupant of the vehicle. The operations may include compare the pose to known risk poses. In addition, the operations may include determine a likelihood and severity of an injury of the occupant based on the comparison. Further, the operations may include, responsive to the likelihood and severity of the injury of the occupant exceeding a threshold value, provide a message to the occupant indicating the occupant should change their pose.

A system may include means to receive, prior to a collision involving a vehicle, first sensor data representative of a first feature of an internal environment of a vehicle. The system may also include means to determine the collision has occurred. In addition, the system may include means to automatically instruct, based on the collision, a sensor to generate second sensor data representative of a second feature of the internal environment of the vehicle. Further, the system may include means to receive the second sensor data from the sensor. The system may include means to determine a severity of the collision based on the first sensor data and the second sensor data.

The system may include means to continuously transmit, responsive to determining the collision has occurred, a severity message to an emergency response center. The severity message may be representative of at least one of the severity of the collision, the first sensor data, the second sensor data, or a state of an occupant of the vehicle.

The means to determine the severity of the collision may include means to compare the first sensor data and the second sensor data to an accident database. The accident database may include accident data corresponding to previous accidents. The accident data may include a diagnosed injury and an accident severity of each of the previous accidents. The means to determine the severity of the collision may also include means to identify a previous accident that is similar to the collision based on the comparison. The severity of the collision may be determined based on the identified previous accident. The severity message may indicate an estimated injury of the occupant based on the diagnosed injury of the identified previous accident.

The system may also include means to identify, prior to the collision, a pose of the occupant of the vehicle. The system may include means to compare the pose to known risk poses. The system may further include means to determine a likelihood and severity of an injury of the occupant based on the comparison. In addition, the system may include, responsive to the likelihood and severity of the injury of the occupant exceeding a threshold value, means to provide a message to the occupant indicating the occupant should change their pose.

Aspects described in the present disclosure may be implemented using computer-readable media for carrying or having computer-executable instructions or data structures stored thereon. Such computer-readable media may be any available media that may be accessed by a general purpose or special purpose computer. By way of example, and not limitation, such computer-readable media may include non-transitory computer-readable storage media including Random Access Memory (RAM), Read-Only Memory (ROM), Electrically Erasable Programmable Read-Only Memory (EEPROM), Compact Disc Read-Only Memory (CD-ROM) or other optical disk storage, magnetic disk storage or other magnetic storage devices, flash memory devices (e.g., solid state memory devices), or any other storage medium which may be used to carry or store desired program code in the form of computer-executable instructions or data structures and which may be accessed by a general purpose or special purpose computer. Combinations of the above may also be included within the scope of computer-readable media.

Computer-executable instructions may include, for example, instructions and data, which cause a general-purpose computer, special purpose computer, or special purpose processing device (e.g., one or more processors) to perform a certain function or group of functions. Although the subject matter has been described in language specific to structural features and/or methodological acts, it is to be understood that the subject matter defined in the appended claims is not necessarily limited to the specific features or acts described above. Rather, the specific features and acts described above are described as example forms of implementing the claims.

As used in the present disclosure, terms used in the present disclosure and especially in the appended claims (e.g., bodies of the appended claims) are generally intended as "open" terms (e.g., the term "including" should be interpreted as "including, but not limited to," the term "having" should be interpreted as "having at least," the term "includes" should be interpreted as "includes, but is not limited to," etc.).

Additionally, if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to aspects containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." or "one or more of A, B, and C, etc." is used, in general such a construction is intended to include A alone, B alone, C alone, A and B together, A and C together, B and C together, or A, B, and C together, etc.

Further, any disjunctive word or phrase presenting two or more alternative terms, whether in the description, claims, or drawings, should be understood to contemplate the possibilities of including one of the terms, either of the terms, or both terms. For example, the phrase "A or B" should be understood to include the possibilities of "A" or "B" or "A and B."

All examples and conditional language recited in the present disclosure are intended for pedagogical objects to aid the reader in understanding the present disclosure and the concepts contributed by the inventor to furthering the art, and are to be construed as being without limitation to such specifically recited examples and conditions. Although aspects of the present disclosure have been described in detail, various changes, substitutions, and alterations could be made hereto without departing from the spirit and scope of the present disclosure.

With respect to the use of substantially any plural or singular terms herein, those having skill in the art can translate from the plural to the singular or from the singular to the plural as is appropriate to the context or application. The various singular/plural permutations may be expressly set forth herein for sake of clarity. A reference to an element in the singular is not intended to mean "one and only one" unless specifically stated, but rather "one or more." Moreover, nothing disclosed herein is intended to be dedicated to the public regardless of whether such disclosure is explicitly recited in the above description.

In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). Furthermore, in those instances where a convention analogous to "at least one of A, B, and C, etc." is used, in general, such a construction is intended in the sense one having skill in the art would understand the convention (e.g., "a system having at least one of A, B, and C" would include but not be limited to systems that include A alone, B alone, C alone, A and B together, A and C together, B and C together, or A, B, and C together, etc.). Also, a phrase presenting two or more alternative terms, whether in the description, claims, or drawings, should be understood to include one of the terms, either of the terms, or both terms. For example, the phrase "A or B" will be understood to include the possibilities of "A" or "B" or "A and B."

The present invention may be embodied in other specific forms without departing from its spirit or essential characteristics. The described aspects are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A driver monitoring system (DMS) comprising:
a memory having computer-readable instructions stored thereon; and
a processor operatively coupled to the memory and configured to read and execute the computer-readable instructions to perform or control performance of operations comprising:
receive, prior to a collision involving a vehicle, first sensor data representative of a first feature of an internal environment of the vehicle;
determine the collision has occurred;
automatically instruct, based on the collision, a sensor to generate second sensor data representative of a second feature of the internal environment of the vehicle;
receive the second sensor data from the sensor;
compare the first sensor data and the second sensor data to accident data corresponding to a plurality of previous accidents, the accident data comprising a diagnosed injury and an accident severity of each previous accident of the plurality of previous accidents; and
determine a severity of the collision based on the comparison.

2. The DMS of claim 1, wherein the operations further comprise continuously transmit, responsive to determining the collision has occurred, a severity message to an emergency response center, the severity message representative of at least one of the severity of the collision, the first sensor data, the second sensor data, or a state of an occupant of the vehicle.

3. The DMS of claim 2, wherein:
the operations further comprise receive an accident database comprising the accident data; and
the operation determine the severity of the collision comprises: identify a previous accident of the plurality of previous accidents that is similar to the collision based on the comparison, wherein the severity of the collision is determined based on the identified previous accident and the severity message further indicates an estimated injury of the occupant based on the diagnosed injury of the identified previous accident.

4. The DMS of claim 1, wherein:
the first feature corresponds to at least one of a pose or a position of an occupant of the vehicle prior to and during the collision; and
the second feature corresponds to a state of the occupant of the vehicle after the collision.

5. The DMS of claim 1, wherein the first feature corresponds to an interior surface of the internal volume, the operation determine the severity of the collision comprises determine a deformity of the interior surface based on a difference between the first feature prior to the collision and the first feature during the collision, wherein the severity of the collision is determined based on the deformity of the interior surface.

6. The DMS of claim 1, wherein:
the first sensor data comprises kinematic information of an occupant of the vehicle, the kinematic information indicates at least one of a direction of a movement of the occupant relative to the vehicle during the collision, a velocity of the movement of the occupant during the collision, a pose of the occupant prior to the collision, a pose of the occupant during the collision, or a deformation of an interior surface of the vehicle during the collision; and
the second sensor data comprises medical information of the occupant, the medical information comprises at least one of a heart rate of the occupant, a body temperature of the occupant, a presence of external bleeding of the occupant, a consciousness state of the occupant, a facial expression of the occupant, a state of a skeletal structure of the occupant, or a respiratory rate of the occupant.

7. The DMS of claim 1, wherein the sensor comprises at least one of a camera, a light detection and ranging sensor, an acoustic sensor, an accelerometer, an RGB-D sensor a heart rate sensor, an infrared sensor, or a respiratory sensor.

8. The DMS of claim 1, wherein the operations further comprise:
identify, prior to the collision, a pose of an occupant of the vehicle;
compare the pose to a plurality of known risk poses;
determine a likelihood and severity of an injury to the occupant based on the comparison; and
responsive to the likelihood and severity of the injury to the occupant exceeding a threshold value, provide a message to the occupant indicating the occupant should change their pose.

9. The DMS of claim 1, wherein the operations further comprise store the first sensor data and the second sensor data in the memory.

10. A non-transitory computer-readable medium having computer-readable instructions stored thereon that are executable by a processor to perform or control performance of operations comprising:
receive, prior to a collision involving a vehicle, first sensor data representative of a first feature of an internal environment of the vehicle;
determine the collision has occurred;
automatically instruct, based on the collision, a sensor to generate second sensor data representative of a second feature of the internal environment of the vehicle;
receive the second sensor data from the sensor;
compare the first sensor data and the second sensor data to accident data corresponding to a plurality of previous accidents, the accident data comprising a diagnosed injury and an accident severity of each previous accident of the plurality of previous accidents; and
determine a severity of the collision based on the comparison.

11. The non-transitory computer-readable medium of claim 10, the operations further comprising continuously transmit, responsive to determining the collision has occurred, a severity message to an emergency response center, the severity message representative of at least one of the severity of the collision, the first sensor data, the second sensor data, or a state of an occupant of the vehicle.

12. The non-transitory computer-readable medium of claim 11, wherein:
the operations further comprise receive an accident database comprising the accident data; and
the operation determine the severity of the collision comprises identify a previous accident of the plurality of previous accidents that is similar to the collision based on the comparison, wherein the severity of the collision is determined based on the identified previous accident and the severity message further indicates an estimated injury of the occupant based on the diagnosed injury of the identified previous accident.

13. The non-transitory computer-readable medium of claim 10, wherein:
the first feature corresponds to at least one of a pose or a position of an occupant of the vehicle prior to and during the collision; and
the second feature corresponds to a state of the occupant of the vehicle after the collision.

14. The non-transitory computer-readable medium of claim 10, wherein the first feature corresponds to an interior surface of the internal volume, the operation determine the severity of the collision comprises determine a deformity of the interior surface based on a difference between the first feature prior to the collision and the first feature during the collision, wherein the severity of the collision is determined based on the deformity of the interior surface.

15. The non-transitory computer-readable medium of claim 10, wherein:
the first sensor data comprises kinematic information of an occupant of the vehicle, the kinematic information indicates at least one of a direction of a movement of the occupant relative to the vehicle during the collision, a velocity of the movement of the occupant during the collision, a pose of the occupant prior to the collision, a pose of the occupant during the collision, or a deformation of an interior surface of the vehicle during the collision; and
the second sensor data comprises medical information of the occupant, the medical information comprises at least one of a heart rate of the occupant, a body temperature of the occupant, a presence of external bleeding of the occupant, a consciousness state of the occupant, a facial expression of the occupant, a state of a skeletal structure of the occupant, or a respiratory rate of the occupant.

16. The non-transitory computer-readable medium of claim 10, wherein the operations further comprise:
identify, prior to the collision, a pose of an occupant of the vehicle;
compare the pose to a plurality of known risk poses;
determine a likelihood and severity of an injury to the occupant based on the comparison; and
responsive to the likelihood and severity of the injury to the occupant exceeding a threshold value, provide a message to the occupant indicating the occupant should change their pose.

17. A system, comprising:
means to receive, prior to a collision involving a vehicle, first sensor data representative of a first feature of an internal environment of the vehicle;
means to determine the collision has occurred;
means to automatically instruct, based on the collision, a sensor to generate second sensor data representative of a second feature of the internal environment of the vehicle;
means to receive the second sensor data from the sensor;
means to compare the first sensor data and the second sensor data to accident data corresponding to a plurality of previous accidents, the accident data comprising a diagnosed injury and an accident severity of each previous accident of the plurality of previous accidents; and
means to determine a severity of the collision based on the comparison.

18. The system of claim 17 further comprising means to continuously transmit, responsive to determining the collision has occurred, a severity message to an emergency response center, the severity message representative of at least one of the severity of the collision, the first sensor data, the second sensor data, or a state of an occupant of the vehicle.

19. The system of claim 18 wherein:
the system further comprises means to receive an accident database comprising the accident data; and
the means to determine the severity of the collision comprises means to identify a previous accident of the plurality of previous accidents that is similar to the collision based on the comparison, wherein the severity of the collision is determined based on the identified previous accident and the severity message further indicates an estimated injury of the occupant based on the diagnosed injury of the identified previous accident.

20. The system of claim 17 further comprising:
means to identify, prior to the collision, a pose of an occupant of the vehicle;
means to compare the pose to a plurality of known risk poses;
means to determine a likelihood and severity of an injury to the occupant based on the comparison; and
responsive to the likelihood and severity of the injury to the occupant exceeding a threshold value, means to provide a message to the occupant indicating the occupant should change their pose.

* * * * *